(12) United States Patent
Ringold

(10) Patent No.: US 8,335,672 B1
(45) Date of Patent: Dec. 18, 2012

(54) SYSTEMS AND METHODS FOR THE IDENTIFICATION OF AVAILABLE PAYERS FOR HEALTHCARE TRANSACTIONS

(75) Inventor: James Morgan Ringold, Lawrenceville, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 178 days.

(21) Appl. No.: 12/732,770

(22) Filed: Mar. 26, 2010

(51) Int. Cl.
*G06Q 40/00* (2012.01)

(52) U.S. Cl. .............................. 703/2; 703/3

(58) Field of Classification Search ............ 705/2–3
See application file for complete search history.

(56) References Cited

U.S. PATENT DOCUMENTS

| | | | |
|---|---|---|---|
| 5,628,530 A | 5/1997 | Thornton | |
| 5,704,044 A | 12/1997 | Tarter et al. | |
| 6,012,035 A | 1/2000 | Freeman et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,606,721 B1 | 10/2009 | Donnelly et al. | |
| 7,617,116 B2 | 11/2009 | Amar et al. | |
| 7,739,132 B2 | 6/2010 | Denny et al. | |
| 7,752,096 B2 | 7/2010 | Santalo et al. | |
| 7,899,688 B2 | 3/2011 | Bonissone et al. | |
| 7,917,378 B2 | 3/2011 | Fitzgerald et al. | |
| 7,996,239 B1 * | 8/2011 | Pellican et al. | 705/2 |
| 2002/0002495 A1 | 1/2002 | Ullman | |
| 2002/0083075 A1 | 6/2002 | Brummel et al. | |
| 2002/0087583 A1 | 7/2002 | Morgan et al. | |
| 2002/0111832 A1 | 8/2002 | Judge | |
| 2002/0147616 A1 | 10/2002 | Pollard et al. | |
| 2002/0147867 A1 | 10/2002 | Satlow | |
| 2002/0188467 A1 | 12/2002 | Eke | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0069760 A1 | 4/2003 | Gelber | |
| 2003/0149625 A1 | 8/2003 | Leonardi et al. | |
| 2003/0154163 A1 | 8/2003 | Phillips et al. | |
| 2003/0171953 A1 | 9/2003 | Narayanan et al. | |
| 2003/0229540 A1 | 12/2003 | Algiene | |

(Continued)

FOREIGN PATENT DOCUMENTS

CA 2482370 A1 3/2006

(Continued)

OTHER PUBLICATIONS

Final Office Action for U.S. Appl. No. 12/242,335 mailed Apr. 26, 2010.

(Continued)

*Primary Examiner* — Valerie Lubin
*Assistant Examiner* — Reginald R Reyes
(74) *Attorney, Agent, or Firm* — Sutherland Asbill & Brennan LLP

(57) ABSTRACT

Systems and methods are provided for the identification of available payers for healthcare transactions. A reply to a healthcare claim transaction may be received from a claims processor computer. Based at least in part on the reply, a determination may be made that the healthcare claim transaction has been rejected for an eligibility reason. An available payer for a patient associated with the received reply may be identified subsequent to the determination. Information associated with the identified available payer may be communicated to a healthcare provider associated with the healthcare claim transaction.

18 Claims, 5 Drawing Sheets

U.S. PATENT DOCUMENTS

| | | |
|---|---|---|
| 2004/0039599 A1 | 2/2004 | Fralic |
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0288972 A1* | 12/2005 | Marvin et al. ............... 705/4 |
| 2006/0020514 A1 | 1/2006 | Yered |
| 2006/0026041 A1 | 2/2006 | Ullman |
| 2006/0080139 A1 | 4/2006 | Mainzer |
| 2006/0149784 A1 | 7/2006 | Tholl et al. |
| 2006/0184391 A1 | 8/2006 | Barre et al. |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0050219 A1 | 3/2007 | Sohr |
| 2007/0136100 A1 | 6/2007 | Daugherty et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0260646 A1 | 11/2007 | Szlam |
| 2007/0282637 A1 | 12/2007 | Smith |
| 2008/0288281 A1 | 11/2008 | Shell et al. |
| 2008/0306952 A1 | 12/2008 | Lynn et al. |
| 2009/0326974 A1 | 12/2009 | Tolan et al. |
| 2010/0161351 A1 | 6/2010 | Howe et al. |

FOREIGN PATENT DOCUMENTS

| | | |
|---|---|---|
| WO | WO 9503569 A3 | 2/1995 |
| WO | WO 0039737 A1 | 7/2000 |
| WO | WO 2007025295 A2 | 3/2007 |

OTHER PUBLICATIONS

Non-final Office Action for U.S. Appl. No. 12/259,889 dated Sep. 8, 2011.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-Final Office Action for U.S. Appl. No. 12/242,355 dated Nov. 9, 2010.

Non-Final Office Action for U.S. Appl. No. 12/650,979 mailed Dec. 12, 2011.

Final Office Action for U.S. Appl. No. 12/259,889, mailed Dec. 14, 2011.

Final Office Action for U.S. Appl. No. 12/650,979 mailed Apr. 23, 2012.

Non-Final Office Action for U.S. Appl. No. 12/259,889 mailed Jun. 15, 2012.

* cited by examiner

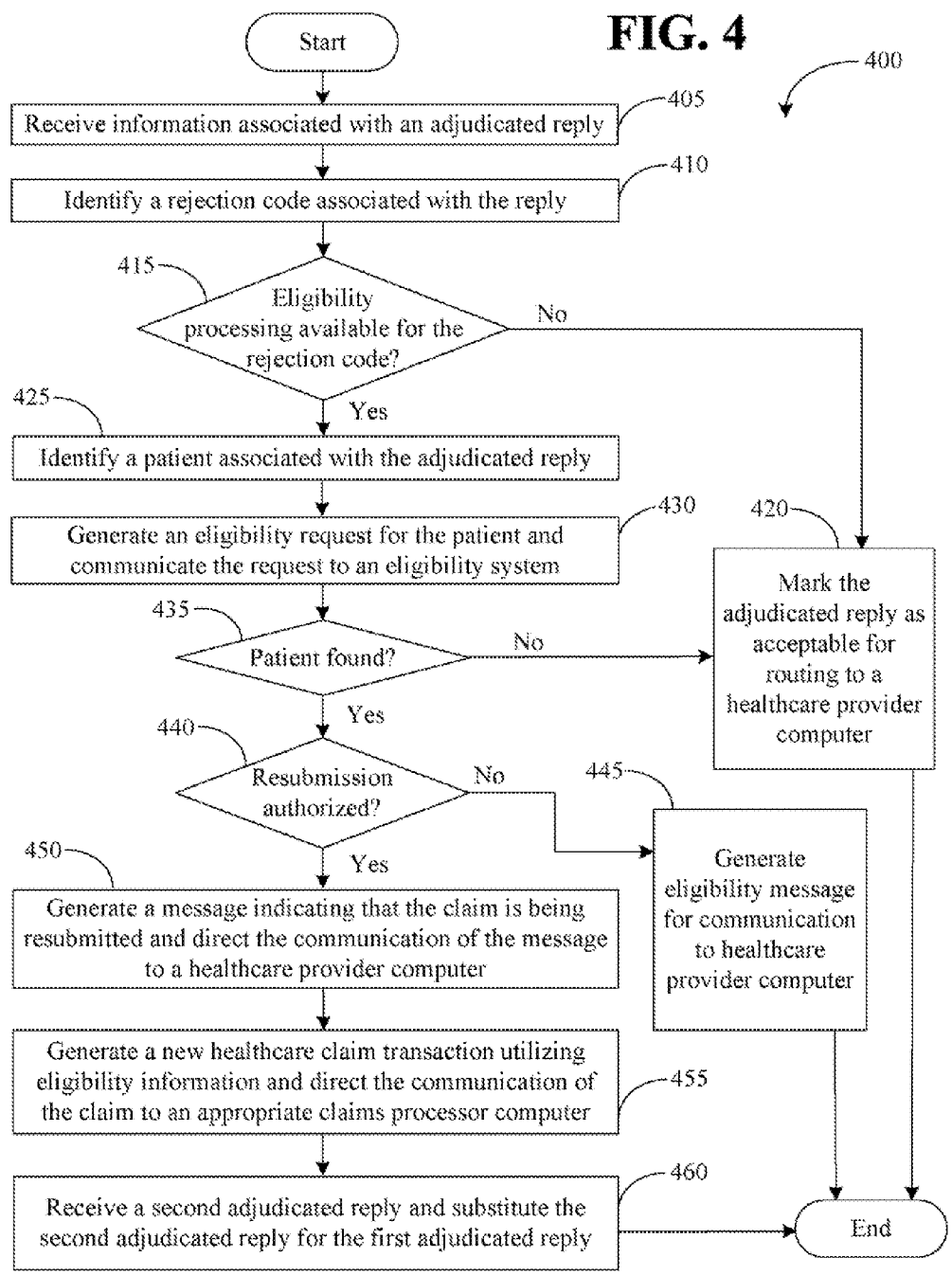

SYSTEMS AND METHODS FOR THE IDENTIFICATION OF AVAILABLE PAYERS FOR HEALTHCARE TRANSACTIONS

FIELD OF THE INVENTION

Aspects of the invention relate generally to healthcare transactions, and more particularly, to the identification of available payers for healthcare transactions.

BACKGROUND OF THE INVENTION

Healthcare providers, such as pharmacies, physicians, and/or hospitals, often generate healthcare claims or healthcare claim transactions that are communicated to appropriate claims processors or payers, such as insurance providers or government payers. When preparing a healthcare claim, a healthcare provider typically identifies a claims processor or payer utilizing coverage information for a patient, such as patient insurance information. However, patients may frequently change insurance plans or information associated with an insurance plan may be updated. A healthcare provider may not be made aware of a change in patient coverage information prior to preparing a healthcare claim, thereby leading to a rejection of the healthcare claim. If the patient is not present at the healthcare provider location, the healthcare provider typically must initiate contact with the patient or wait for the patient to arrive in order to reprocess the rejected healthcare claim. These delays often result in the expenditure of additional time and resources on the part of the healthcare provider. Additionally, delays on the part of the patient, such as delays in having prescriptions filled, may result from the rejection of the healthcare claim, thereby leading to decreased patient satisfaction.

Therefore, systems and methods for the identification of available payers for healthcare transactions are desirable.

BRIEF DESCRIPTION OF THE INVENTION

Some or all of the above needs and/or problems may be addressed by certain embodiments of the invention. Embodiments of the invention may include systems, methods, and apparatus for the identification of available payers for healthcare transactions. In one embodiment, a method for the identification of an available payer for a healthcare transaction is provided. A reply to a healthcare claim transaction may be received from a claims processor computer. Based at least in part on the reply, a determination may be made that the healthcare claim transaction has been rejected for an eligibility reason. An available payer for a patient associated with the received reply may be identified subsequent to the determination. Information associated with the identified available payer may be communicated to a healthcare provider associated with the healthcare claim transaction. In certain embodiments, the operations may be performed by one or more computers associated with a service provider.

In accordance with another embodiment of the invention, a system for the identification of an available payer for a healthcare transaction may be provided. The system may include at least one memory and at least one processor. The at least one memory may be operable to store computer-executable instructions. The at least one processor may be configured to access the at least one memory and execute the computer-executable instructions to: receive a reply to a healthcare claim transaction from a claims processor computer; determine, based at least in part on the reply, that the healthcare claim transaction has been rejected for an eligibility reason; identify, subsequent to the determination, an available payer for a patient associated with the received reply; and direct the communication of information associated with the identified available payer to a healthcare provider associated with the healthcare claim transaction.

In accordance with yet another embodiment of the invention, a method for the identification of an available payer for a healthcare transaction may be provided. A reply to a healthcare claim transaction may be received from a claims processor computer. Based at least in part upon a determination that the healthcare claim transaction has been rejected, an eligibility request for a patient associated with the healthcare claim transaction may be generated, and the eligibility request may be communicated to an eligibility system. Based at least in part upon a response to the eligibility request received from the eligibility system, an available payer for the patient may be identified. Information associated with the identified available payer may be communicated to a healthcare provider associated with the healthcare claim transaction. In certain embodiments, the operations may be performed by one or more computers associated with a service provider.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein:

FIG. 4 is a flow diagram of an example method for processing a reply to a healthcare claim transaction in order to identify an available payer for the healthcare claim transaction, according to an example embodiment of the invention.

DETAILED DESCRIPTION

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems, methods, and apparatus for the identification of available payers for healthcare transactions. In one embodiment, a reply to a healthcare claim transaction may be received by a service provider from a claims processor or a payer. Based at least in part on the reply, the service provider may determine that the healthcare claim transaction has been rejected by the claims processor for an eligibility reason. In other words, the service provider may determine that the healthcare claim transaction has been rejected because the patient is either not covered by the claims processor or incorrect coverage information was included in the healthcare claim transaction. As one example, a rejection code included in the reply may be compared to one or more stored rejection codes for eligibility-based rejections, and a determination may be made that the claim transaction was rejected for an eligibility reason if a match is found. Based upon the determination, an available payer for a patient associated with or identified by the received reply and/or the underlying claim transaction may be identified. For example, an eligibility request (e.g., an E1 request) may be communicated to an eligibility system, and an available payer for the patient may be identified based upon a received response to the eligibility request. As another example, a database of eligibility information may be searched for an available payer of the patient. Once an available payer has been identified, information associated with the identified available payer may be communicated to a healthcare provider associated with the healthcare claim transaction. For example, information associated with the available payer may be appended to the reply, and the reply may be communicated to the healthcare provider. As another example, a separate message with information associated with the available payer may be communicated to the healthcare provider. Additionally, in certain embodiments, a second healthcare claim transaction may be automatically generated and communicated to the identified available payer.

System Overview

Figure 1:
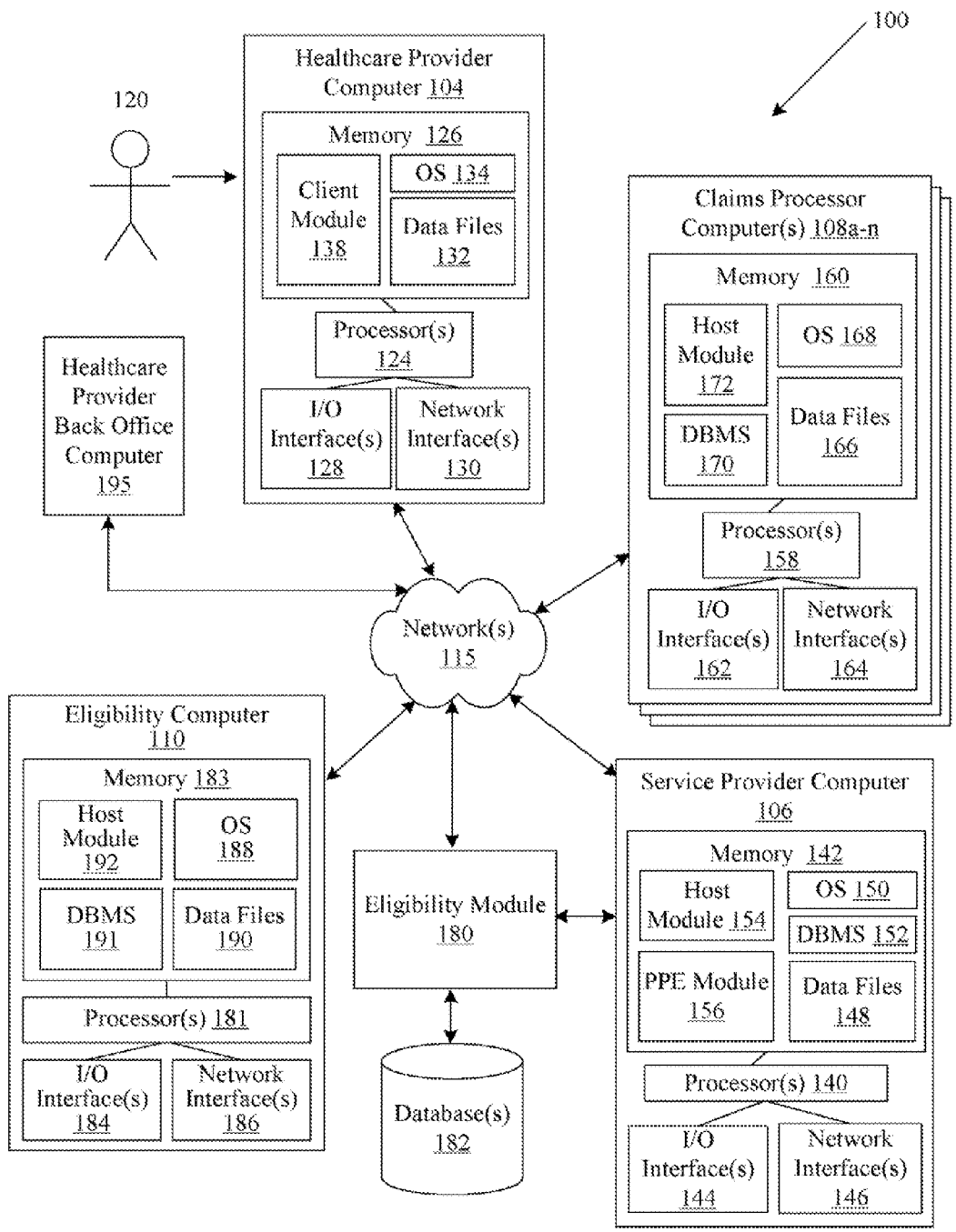
FIG. 1 illustrates an example overview of a system that facilitates the identification of available payers for healthcare transactions, according to an example embodiment of the invention.

An example system 100 for facilitating the identification of available payers for healthcare transactions will now be described illustratively with respect to FIG. 1. As shown in FIG. 1, the system 100 may include one or more healthcare provider computers 104, service provider computers 106, claims processor computers 108*a-n*, and eligibility computers 110. As desired, each of the healthcare provider computer 104, service provider computer 106, claims processor computers 108*a-n*, and eligibility computer 110 may include one or more processing devices that may be configured for accessing and reading associated computer-readable media having stored thereon data and/or computer-executable instructions for implementing the various methods of the invention.

Additionally, in certain embodiments, the service provider computer 106 may include or otherwise be in communication with an eligibility module 180 or an eligibility application, which may access and/or be in communication with one or more suitable data storage devices 182 and/or databases. The eligibility module 180 may receive information associated with a reply or response, such as an adjudicated reply, to a healthcare claim transaction. Based upon a determination by the eligibility module 180 that the healthcare claim transaction has been rejected by a claims processor or payer for an eligibility reason, the eligibility module may facilitate the identification of an available payer for a patient associated with the healthcare claim transaction. In certain embodiments, the eligibility module 180 may communicate with the eligibility computer 110 in order to identify an available payer. Once an available payer has been identified, the eligibility module 180 may direct the communication of information associated with the available payer to a healthcare provider that submitted the healthcare claim transaction. Additionally, in certain embodiments, the eligibility module 180 may facilitate the generation of a new or second healthcare claim transaction to be routed or otherwise communicated to the available payer. As desired, the eligibility module 180 may substitute the second healthcare claim transaction for the rejected healthcare claim transaction.

Generally, network devices and systems, including one or more of the healthcare provider computer 104, service provider computer 106, claims processor computers 108*a-n*, and eligibility computer 110 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, claims processor computers 108*a-n*, and eligibility computer 110 may be in communication with each other via one or more networks, such as network 115, which as described below can include one or more separate or shared private and public networks, including the Internet or a publicly switched telephone network. Each of these components—the healthcare provider computer 104, service provider computer 106, and claims processor computers 108*a-n*, and the network 115—will now be discussed in further detail.

The healthcare provider computer 104 may be associated with a healthcare provider, for example, a pharmacy, physician's office, hospital, etc. The healthcare provider computer 104 may be any suitable processor-driven device that facilitates the processing of healthcare requests (e.g., prescription orders) made by or on behalf of patients or consumers and the communication of information associated with healthcare transaction requests (e.g., healthcare claim transactions, healthcare claim requests, eligibility transaction requests, etc.) to the service provider computer 106. For example, the healthcare provider computer 104 may be a computing device that includes any number of server computers, mainframe computers, networked computers, desktop computers, personal computers, digital assistants, personal digital assistants, digital tablets, Internet appliances, application-specific circuits, microcontrollers, minicomputers, and/or any other processor-based device(s). In certain embodiments, the healthcare provider computer 104 may be a suitable point of sale device associated with a healthcare provider. The execution of the computer-implemented instructions by the healthcare provider computer 104 may form a special purpose computer or other particular machine that is operable to facilitate the processing of healthcare requests (e.g., prescription orders) made by or on behalf of patients and the communication of information associated with healthcare transaction requests (e.g., claim requests and/or healthcare claim transactions, eligibility transaction requests, etc.) to a service provider computer 106. Additionally, in certain embodiments of the invention, the operations and/or control of the healthcare provider computer 104 may be distributed among several processing components.

In addition to having one or more processors 124, the healthcare provider computer 104 may include one or more memory devices 126, one or more input/output ("I/O") interface(s) 128, and one or more network interface(s) 130. The memory devices 126 may be any suitable memory device(s), for example, caches, read only memory devices, random access memory devices, magnetic storage devices, removable storage devices, etc. The memory devices 126 may store data, executable instructions, and/or various program modules utilized by the healthcare provider computer 104, for example, data files 132, an operating system 134, and/or a client module 138. The data files 132 may include any suitable data that facilitates the receipt and/or processing of healthcare requests (e.g., prescription orders) by the healthcare provider computer 104 and the generation and/or processing of healthcare transaction requests (e.g., healthcare claim requests, healthcare claim transactions, eligibility transaction requests, etc.) that are communicated to the service provider computer 106. For example, the data files 132 may include, but are not limited to, healthcare information and/or contact information associated with one or more patients, information associated with the service provider computer 106, information associated with one or more claims processors or payers, information associated with one or more healthcare transaction requests, and/or information associated with the generation of healthcare claim requests. The operating system ("OS") 134 may be a suitable software module that controls the general operation of the healthcare provider computer 104. The OS 134 may also facilitate the execution of other software modules by the one or more processors 124, for example, the client module 138. The OS 134 may be, but is not limited to, Microsoft Windows®, Apple OSX™, Linux, Unix, or a mainframe operating system. The client module 138 may be an Internet browser or other software, including a dedicated program, for interacting with the service provider computer 106. For example, a user such as a pharmacist or other pharmacy employee, may utilize the client module 138 in preparing and providing a prescription claim request to the service provider computer 106 for delivery to one or more appropriate claims processor computers 108, for adjudication or other coverage/benefits determination. The healthcare provider computer 104 may also utilize the client module 138 to retrieve or otherwise receive data, messages, or responses from the service provider computer 106 and/or other components of the system 100.

In operation, the healthcare provider computer 104 may receive information associated with a healthcare request (e.g., prescription order) from a patient. As one example, the healthcare provider computer 104 may receive information associated with a healthcare request for a patient at a point of sale, such as in a pharmacy during a prescription fulfillment or purchase transaction or at a physician's office during the provision of a healthcare service. As another example, the healthcare provider computer 104 may electronically receive a healthcare request from a physician computer, a patient computer, or other patient device. The healthcare provider computer 104 may generate a healthcare transaction request (e.g., healthcare claim request, healthcare claim transaction, eligibility transaction request, etc.), and information associated with the healthcare transaction request may be communicated to the service provider computer 106. The healthcare provider computer 104 may then receive one or more responses to the healthcare transaction requests, such as an adjudicated reply for a claim transaction, a rejection message associated with a transaction, and/or one or more messages generated by the service provider computer 106 and/or the eligibility module 180.

The one or more I/O interfaces 128 may facilitate communication between the healthcare provider computer 104 and one or more input/output devices, for example, one or more user interface devices, such as a display, keypad, control panel, touch screen display, remote control, microphone, etc. that facilitate user interaction with the healthcare provider computer 104. For example, the one or more I/O interfaces 128 may facilitate entry of information associated with a healthcare transaction request (e.g., healthcare claim transaction, healthcare claim request, eligibility transaction request, etc.) by an employee of a healthcare provider, such as a pharmacy employee. The one or more network interfaces 130 may facilitate connection of the healthcare provider computer 104 to one or more suitable networks, for example, the network 115 illustrated in FIG. 1. In this regard, the healthcare provider computer 104 may receive and/or communicate information to other network components of the system 100, such as the service provider computer 106.

In certain embodiments, the healthcare provider computer 104 can further include a facsimile/printing device operative to receive and print one or more messages received from the service provider computer 106 and/or the eligibility module 180. For example, as described further below, the service provider computer 106 may on occasion transmit a facsimile or other printing command to the healthcare provider computer 104 and/or the facsimile/printing device containing one or more messages associated with available payers for patients and/or the resubmission of healthcare claim transactions to available payers. The transmission from the service provider computer 106 may be directly to the facsimile/printing device, such as may be accomplished via a network 115 (e.g., Internet, cellular network, wireless network, or any other similar network, etc.). In another embodiment, the transmission may be to the healthcare provider computer 104, which in turn communicates with and commands the facsimile/printing device to print a message. Although the term facsimile/printing device is used throughout this description, it is appreciated that any other device operable to receive and print or generate a display of a notification message may be included within the scope of a facsimile/printing device. Examples of other devices include, but are not limited to, a mobile device (e.g., cellular telephone, personal digital assistant, personal information device, etc.), a personal computer, a computer kiosk, or any other handheld or mobile devices.

With continued reference to FIG. 1, the service provider computer 106 may include, but is not limited to, any suitable processor-driven device that is configured for receiving, processing, and fulfilling requests from the healthcare provider computer 104 and/or claims processor computers 108*a-n* relating to prescription, pharmacy, benefits, eligibility, and/or healthcare transactions and/or other activities. In certain embodiments, the service provider computer 106 may be a switch/router that routes healthcare transactions comprising requests and replies/responses. For example, the service provider computer 106 may route billing requests and/or prescription claim requests communicated from the healthcare provider computer 104 to one or more claims processor computers 108*a-n*, which may be associated with pharmacy benefits managers (PBM), insurers, government payers, or claims clearinghouses. The healthcare provider computer 104 may then route adjudicated replies or other responses to the claim requests from the claims processor computer 108 to the healthcare provider computer 104. In certain embodiments, the service provider computer 106 may include a suitable host server, host module, or other software that facilitates the receipt of a healthcare transaction request or reply and/or the routing of the transaction request or reply to a recipient. Any number of healthcare provider computers and/or claims processor computers may be in communication with the service provider computer 106 as desired in various embodiments of the invention.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors associated with the service provider computer 106 to form a special purpose computer or other particular machine that is operable to facilitate the receipt, routing, and/or processing of healthcare claim requests or healthcare claim transactions. The one or more processors that control the operations of the service provider computer 106 may be incorporated into the service provider computer 106 and/or may be in communication with the service provider computer 106 via one or more suitable networks. In certain embodiments of the invention, the operations and/or control of the service provider computer 106 may be distributed among several processing components.

Similar to the healthcare provider computer 104, the service provider computer 106 may include one or more processors 140, one or more memory devices 142, one or more input/output ("I/O") interface(s) 144, and one or more network interfaces 146. The one or more memory devices 142 may be any suitable memory device(s), for example, caches, read only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a pre- and post-edit ("PPE") module 156, and a database management system ("DBMS") 152 to facilitate management of data files 148 and other data stored in the memory devices 142 and/or one or more databases or data storage devices 182. The OS 150 may be, but is not limited to, Microsoft Windows®, Apple OSX™, Linux, Unix, or a mainframe operating system. The OS 150 may be a suitable software module that controls the general operation of the service provider computer 106 and/or that facilitates the execution of other software modules.

The PPE module 156 may be operable to perform one or more pre-edits on a received healthcare transaction, such as a claim transaction, prior to routing or otherwise communicating the received healthcare transaction to a recipient, such as a claims processor computer 108. Additionally, the PPE module 156 may be operable to perform one or more post-edits on an adjudicated reply or response that is received from a claims processor computer 108 for a healthcare claim transaction prior to routing the adjudicated reply to the healthcare provider computer 104. A wide variety of different pre-edits and/or post-edits may be performed as desired in various embodiments of the invention. In certain embodiments, the eligibility module 180 may be incorporated into the PPE module 156 and/or in communication with the PPE module 156. As desired, the PPE module 156 may selectively invoke the eligibility module 180 in order to process adjudicated replies for healthcare claim transactions.

According to an embodiment of the invention, the data files 148 may store healthcare transaction records associated with communications received from various healthcare provider computers 104 and/or various claims processor computers 108a-n. The data files 148 may also store any number of suitable routing tables that facilitate determining the destination of communications received from a healthcare provider computer 104 or claims processor computer 108a-n and/or the destination of claims generated by the eligibility module 180. The host module 154 may receive, process, and respond to requests from the client module 138 of the healthcare provider computer 104, and may further receive, process, and respond to requests of the respective host modules 172 of the various claims processor computers 108a-n. The service provider computer 106 may include additional program modules for performing other processing methods described herein. Those of ordinary skill in the art will appreciate that the service provider computer 106 may include alternate and/or additional components, hardware or software without departing from example embodiments of the invention.

An eligibility module 180 or eligibility application may also be operative with the service provider computer 106. The eligibility module 180 may include computer-executable instructions for identifying or otherwise determining an available payer for a healthcare claim transaction that has been rejected. In certain embodiments, the processing performed by the module 180 may be a post-edit service that is performed for an adjudicated reply. If an eligibility service is enabled for a healthcare provider associated with the healthcare provider computer 104, then the eligibility module 180 may process a received adjudicated reply for a claim transaction that was previously routed to a claims processor computer 108.

In operation, the eligibility module 180 may receive information associated with a response or reply to a healthcare claim transaction, such as an adjudicated reply, and the eligibility module 180 may determine whether the claim has been paid or approved by a claims processor that processed the claim. If it is determined that the claim has been rejected, then the eligibility module 180 may further process the response in an attempt to identify an available payer for a patient associated with the healthcare claim transaction. As an alternative to the eligibility module determining whether the healthcare claim transaction was rejected, the eligibility module 180 may be selectively invoked based upon a determination by the PPE module 156 that the claim has been rejected.

Once invoked, the eligibility module 180 may determine whether the healthcare claim transaction was rejected due to an eligibility reason. In other words, the eligibility module 180 may determine whether the healthcare claim transaction was rejected because the patient is either not covered by the claims processor or incorrect coverage information for the patient was included in the claim. In certain embodiments, the determination of whether the claim was rejected due to an eligibility reason may be based upon an analysis of one or more reject or rejection codes included in the claim. A wide variety of eligibility-based rejection codes may be utilized as desired in various embodiments of the invention, such as one or more suitable National Council for Prescription Drug Programs ("NCPDP") rejection codes. In one example embodiment, a rejection code included in the response may be identified and compared to one or more stored rejection codes associated with eligibility-based rejections. In certain embodiments, the stored rejection codes may be standard NCPDP rejection codes. In other embodiments, the stored rejection codes may be claims processor specific. One example of suitable NCPDP rejection codes that may be stored is set forth in Table 1 below:

TABLE 1

Example Rejection Codes

| Rejection Code | Reason for Rejection |
| --- | --- |
| 01 | Missing or incomplete Banking Identification Number (BIN) |
| 06 | Missing or incomplete Group Number |
| 07 | Missing or incomplete Cardholder Identifier |
| 41 | Indication that the claim should be submitted to another processor |
| 51 | Non-matched or unmatched Group Number |
| 52 | Non-matched or unmatched Cardholder Identifier |
| 65 | An indication that the patient is not covered |
| 68 | An indication that the prescription is being filled after coverage has expired |

Any number of other rejection codes may be stored and/or utilized as desired in various embodiments of the invention. If the eligibility module 180 identifies a match between the rejection code included in a response and a stored rejection code associated with an eligibility-based rejection, then the eligibility module 180 may determine that the claim has been rejected for an eligibility reason. Other suitable methods may be utilized as desired in various embodiments to determine that a claim has been rejected for an eligibility reason.

Once a determination has been made that the claim has been rejected for an eligibility reason, the eligibility module 180 may attempt to identify an available payer (e.g., claims processor, insurance provider, government payer, etc.) for a patient identified by or otherwise associated with the healthcare claim transaction or response. In certain embodiments, the eligibility module 180 may search a database or other data repository of eligibility information utilizing patient identifying information (e.g., patient name, patient identifier, etc.) in an attempt to locate stored eligibility information for the patient and/or one or more available payers for the patient. In other embodiments, the eligibility module 180 may generate an eligibility request (e.g., an E1 request) that includes at least the patient information from the healthcare transaction request and/or response. The eligibility request can be delivered to an eligibility computer 110 or eligibility system for processing. If the eligibility computer 110 identifies one or more payers available for the patient, then the eligibility computer 110 may provide an eligibility response that identifies the one or more payers. For example, the one or more payers may be identified in the eligibility response according to one or both of a respective name or a Banking Identification Number ("BIN")/Processor Control Number ("PCN"). The eligibility response may also identify a priority, ordering, or ranking among the payers if more than two payers are identified. The priority, ordering, or ranking may be used to determine an order in which claim requests are generated and processed by the two or more identified payers. On the other hand, if the eligibility computer 110 cannot identify any payers associated with the patient, then the eligibility response received by the eligibility module 180 may reflect that no payers have been identified for the patient. In an alternative embodiment of the invention, the eligibility module 180 may perform similar processing and the eligibility computer 110 may not be needed. In another alternative embodiment, the eligibility module 180 may send eligibility requests to multiple eligibility computers 110, and thus, multiple eligibility responses may be received.

If an eligibility response indicates that the patient was not found or that no available payers have been identified, then the eligibility module 180 may direct the service provider computer 106 to route, to the healthcare provider computer 104, the response or reply for the healthcare claim indicating that the claim has been rejected. If, however, an eligibility response or accessed eligibility information indicates that the patient was found or that a payer is available for the patient, then the eligibility module 180 may communicate information associated with one or more available payers to the healthcare provider computer 104 and/or to other devices associated with the healthcare provider computer 104, such as a suitable facsimile/printer device. In this regard, a healthcare provider may receive an indication that the original claim has been rejected due to an eligibility reason and information associated with an available payer for the patient. In certain embodiments, the available payer may be the same payer identified by the healthcare claim transaction, and correct and/or updated coverage information for the patient may be provided. In other embodiments, the available payer may be a different payer than the payer identified by the healthcare claim transaction. A wide variety of information associated with the available payer may be provided to the healthcare provider as desired in various embodiments of the invention, including but not limited to, a payer name, a BIN, a Group number, a Cardholder Identifier of the patient, etc. In certain embodiments, the information associated with one or more available payers may be appended to the response or reply to the healthcare claim transaction, and the response may be routed or otherwise communicated to the healthcare provider computer 104. In other embodiments, the information associated with one or more available payers may be communicated to the healthcare provider via one or more separate messages. As a result of communicating available payer information to a healthcare provider, the healthcare provider may update records and/or coverage information for the patient. As desired, the healthcare provider may additionally generate and submit a new or updated healthcare claim transaction for communication to the identified available payer. In this regard, healthcare provider delays may be reduced and customer satisfaction may be enhanced.

In certain embodiments, the eligibility module 180 may determine whether automatic resubmissions have been enabled for the healthcare provider in situations where an available payer has been identified. For example, the eligibility module 180 may access preferences associated with the healthcare provider or a group of healthcare providers, and determine whether the healthcare claim transaction should be resubmitted to an identified available payer. When an automatic resubmission is enabled, the eligibility module 180 may generate a second healthcare claim transaction utilizing information included in the rejected claim transaction, the reply to the rejected claim, and/or the information associated with the available payer. The eligibility module 180 may direct the service provider computer 106 to route or otherwise communicate the generated second healthcare claim transaction to a claims processor computer 108 associated with the available payer. In certain embodiments, a determination of whether to generate and communicate a second claim may additionally be based on one or more timing parameters and/or response time thresholds associated with the healthcare provider or a group of healthcare providers.

Additionally, as desired, a message indicating that the healthcare claim transaction has been resubmitted may be generated by the eligibility module 180 and communicated to the healthcare provider. Following communication of the second healthcare claim transaction to a claims processor computer 108 of the available payer, a second response or reply to the second healthcare claim transaction may be received from the claims processor computer 108. The service provider computer 106 and/or the eligibility module 180 may route or otherwise communicate the received second response to the healthcare provider computer 104. In certain embodiments, the first response may be replaced by the second response such that a single response is routed to the healthcare provider computer 104. If a substitution or replacement is made, an indication that the claim was resubmitted may also be communicated to the healthcare provider, either as additional information included in the second response or as a separate message. In this regard, the healthcare provider may determine that the submitted coverage information for the patient was incorrect, and the healthcare provider may update its records for the healthcare claim and/or for the patient.

The data storage devices 182 may be operable to store data as well as information associated with various rules, parameters, and/or edits that may be utilized by the eligibility module 180 to process adjudicated replies. Examples of data that may be stored include, but are not limited to, patient coverage information, information associated with one or more eligibility computers 110 or eligibility systems, information associated with eligibility requests, etc. In certain embodiments, rules may be received from one or more other components of the system 100, such as the healthcare provider computer 104, and/or the healthcare provider back office computer 195, and at least a portion of the received rules may be stored. A wide variety of rules and/or other information may be stored, including but not limited to, automatic resubmission preferences and/or rules associated with preferences for receiving available payer information. In addition to or as an alternative to utilizing certain rules associated with a healthcare provider or group of healthcare providers, one or more default rules may be accessed and utilized by the eligibility module 180. Additionally, the data storage devices 182 may be operable to store information associated with healthcare claim transactions, adjudicated replies, and/or processing performed by the eligibility module 180, including but not limited to, information extracted from healthcare claim transactions and/or adjudicated replies, information associated with generated messages and/or reversal requests, etc. In certain embodiments, the data storage devices 182 may additionally store billing information associated with the healthcare claim transactions and/or reports associated with the healthcare claim transactions and/or processing of the healthcare claim transactions. The data storage devices 182 may be accessible by the eligibility module 180 and/or the service provider computer 106.

In certain embodiments, the eligibility module 180 and/or the service provider computer 106 may be operable to generate one or more reports that are associated with processed healthcare claim transactions, adjudicated replies, eligibility requests, and/or identification of available payers. A wide variety of different types of reports may be generated as desired in various embodiments of the invention. Additionally, a wide variety of different information may be incorporated into generated reports, including but not limited to, available payers for a patient, a number of times the eligibility module 180 was invoked for a healthcare provider or group of healthcare providers (e.g., a pharmacy chain), information associated with the results of various processing performed by the eligibility module 180, date information and/or date range information associated with the processed healthcare claim transactions and/or replies, financial information associated with the healthcare claim transactions and/or replies, and/or billing information associated with the invocation of the eligibility module 180. Reports may be sorted or formatted utilizing a wide variety of different criteria, parameters, and/or techniques. Additionally, the eligibility module 180 may communicate or direct the communication of generated reports to one or more other components of the system 100, for example, the healthcare provider computer 104 and/or a healthcare provider back office computer 195 associated with a group of healthcare providers.

A wide variety of different techniques and/or software programs may be utilized to format a generated report. For example, a report may be formatted as a comma-separated-value ("csv") file, as a spreadsheet file, as a word processor file, as a text file, etc. Additionally, a wide variety of different communication techniques may be utilized to communicate a report to the recipient, including but not limited to, email, short message service ("SMS") messaging, other electronic communications, snail mail, etc. A report may be pushed to a recipient by the eligibility module 180 or other reporting module, or, alternatively pulled from the eligibility module 180 by a recipient submitting a request for one or more reports. Additionally, in certain embodiments, a report may be made available for download from an appropriate web site or server, such as a web site hosted by the service provider computer 106.

Messages and/or reports (e.g., transaction reports and/or other reports) that are generated by the eligibility module 180 may be communicated to a recipient (e.g., the healthcare provider computer 104, the healthcare provider back office computer 195, etc.) by the eligibility module 180 in either a direct or indirect manner. In certain embodiments, messages and/or reports may be directly communicated to a recipient by the eligibility module 180 via one or more suitable networks 115. In other embodiments, the messages and/or reports may be communicated by the eligibility module 180 to another component of the system 100, such as the service provider computer 106, for communication to a recipient. For messages and/or reports that are communicated to a healthcare provider, the communications may be sent to the healthcare provider computer 104 and/or to another device associated with the healthcare provider, such as a facsimile/printer device.

The operations of the eligibility module 180 and/or the data storage devices 182 are described in greater detail below with reference to FIGS. 3-4.

With continued reference to the service provider computer 106, the one or more I/O interfaces 144 may facilitate communication between the service provider computer 106 and one or more input/output devices, for example, one or more user interface devices, such as a display, keypad, control panel, touch screen display, remote control, microphone, etc. that facilitate user interaction with the service provider computer 106. The one or more network interfaces 146 may facilitate connection of the service provider computer 106 to one or more suitable networks, for example, the network 115 illustrated in FIG. 1. In this regard, the service provider computer 106 may communicate with other components of the system 100.

With continued reference to FIG. 1, any number of claims processor computers 108a-n may be provided. Each claims processor computer (generally referred to as claims processor computer 108) may be any suitable processor-driven device that facilitates receiving, processing, and/or fulfilling healthcare claim transactions and/or healthcare claim requests received from the service provider computer 106. For example, a claims processor computer 108 may be a processor-driven device associated with a pharmacy benefits manager ("PBM"), an insurer, a government payer, or a claims clearinghouse. As desired, the claims processor computer 108 may include any number of special purpose computers or other particular machines, application-specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare claim transaction requests received from the service provider computer 106. The one or more processors that control the operations of the claims processor computer 108 may be incorporated into the claims processor computer 108 and/or in communication with the claims processor computers 108 via one or more suitable networks. In certain embodiments of the invention, the operations and/or control of the claims processor computer 108 may be distributed amongst several processing components.

Similar to other components of the system 100, each claims processor computer 108 may include one or more processors 158, one or more memory devices 160, one or more input/output ("I/O") interface(s) 162, and one or more network interfaces 164. The one or more memory devices 160 may be any suitable memory device(s), for example, caches, read only memory devices, random access memory devices, magnetic storage devices, removable memory devices, etc. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare claim transactions, for example, patient profiles, patient insurance information, other information associated with a patient, information associated with a healthcare provider, etc. The OS 168 may be a suitable software module that controls the general operation of the claims processor computer 108. The OS 168 may also facilitate the execution of other software modules by the one or more processors 158, for example, the DBMS 170 and/or the host module 172. The OS 168 may be, but is not limited to, Microsoft Windows®, Apple OSX™, Linux, Unix, or a mainframe operating system. The DBMS 170 may be a suitable software module that facilitates access and management of one or more databases that are utilized to store information that is utilized by the claims processor computer 108 in various embodiments of the invention. The host module 172 may initiate, receive, process, and/or respond to requests, such as healthcare claim transactions or claim requests, from the host module 154 of the service provider computer 106. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the invention.

The one or more I/O interfaces 162 may facilitate communication between the claims processor computer 108 and one or more input/output devices, for example, one or more user interface devices, such as a display, keypad, control panel, touch screen display, remote control, microphone, etc. that facilitate user interaction with the claims processor computer 108. The one or more network interfaces 164 may facilitate connection of the claims processor computer 108 to one or more suitable networks, for example, the network 115 illustrated in FIG. 1. In this regard, the claims processor computer 108 may receive healthcare claim transactions and/or other communications from the service provider computer 106, and the claims processor computer 108 may communicate information associated with processing claim transactions to the service provider.

With continued reference to FIG. 1, one or more eligibility computers 110 may be provided. The eligibility computer 110 may be any suitable processor-driven device that may determine whether one or more payers are available for one or more patients. In this regard, the eligibility computer 110 may receive eligibility requests for one or more patients, and respond with information regarding any payers available for the one or more patients. For example, the eligibility computer may be a processor-driven device associated with an eligibility service provider, a data management provider, or one or more payers. As desired, the eligibility computer 110 may include any number of special purpose computers or other particular machines, application-specific circuits, microcontrollers, personal computers, minicomputers, mainframe computers, servers, and the like. In certain embodiments, the operations of the eligibility computer 110 may be controlled by computer-executed or computer-implemented instructions that are executed by one or more processors associated with the eligibility computer 110 to form a special purpose computer or other particular machine that is operable to facilitate the receipt and processing of eligibility requests received from the service provider computer 106 or another computer. The one or more processors that control the operations of the eligibility computer 110 may be incorporated into the eligibility computer 110 and/or in communication with the eligibility computer 110 via one or more suitable networks. In certain embodiments of the invention, the operations and/or control of the eligibility computer 110 may be distributed among several processing components.

Similar to other components of the system 100, the eligibility computer 110 may include one or more processors 181, one or more memory devices 183, one or more I/O interfaces 184, and/or one or more network interfaces 186. The one or more memory devices 183 may be any suitable memory device(s), for example, caches, read only memory devices, random access memory devices, magnetic storage devices, removable memory devices, etc. The one or more memory devices 183 may store data, executable instructions, and/or various program modules utilized by the eligibility computer 110, for example, data files 190, an operating system ("OS") 188, a database management system ("DBMS") 191, and a host module 192. The data files 190 may include any suitable information that is utilized by the eligibility computer 110 to process eligibility requests, for example, patient profiles, patient insurance information, payer information, other information associated with a patient, information associated with a healthcare provider, etc. In addition, the data files 190 may aggregate payer information for each patient such that a plurality of payers may be identified for each patient. It will be appreciated that the same or similar information as provided by the data files 190 could likewise be stored in a data storage device 182, as described herein. Likewise, in some example embodiments of the invention, the eligibility computer 110 could likewise be implemented as part of the service provider computer 106 and/or the eligibility module 180 without departing from example embodiments of the invention. In yet another alternative embodiment of the invention, the eligibility computer 110 could also be implemented as part of another entity or processor that is designed to receive and respond to eligibility requests.

Still referring to the eligibility computer 110, the operating system ("OS") 188 may be a suitable software module that controls the general operation of the eligibility computer 110.

The OS 188 may also facilitate the execution of other software modules by the one or more processors 181, for example, the DBMS 191 and/or the host module 192. The OS 188 may be, but is not limited to, Microsoft Windows®, Apple OSX™, Linux, Unix, or a mainframe operating system. The DBMS 191 may be a suitable software module that facilitates access and management of one or more databases that are utilized to store information that is utilized by the eligibility computer 110 in various embodiments of the invention. The host module 192 may initiate, receive, process, and/or respond to requests, such as eligibility requests, from the host module 154 of the service provider computer 106 or the eligibility module 180. The eligibility computer 110 may include additional program modules for performing other pre-processing or post-processing methods described herein. Those of ordinary skill in the art will appreciate that the eligibility computer 110 may include alternate and/or additional components, hardware or software without departing from example embodiments of the invention.

The healthcare provider back office computer 195 may be one or more computers associated with a group of healthcare providers, such as a chain of pharmacies. The healthcare provider back office computer 195 may components that are similar to those of other devices included in the system 100, such as the healthcare provider computer 104. For example, the healthcare provider back office computer 195 may be a processor-driven device that is operable or configured to receive reports and/or billing information associated with the processing of healthcare claim transactions by the eligibility module 180. Additionally, as desired, the healthcare provider back office computer 195 may be operable or configured to provide various rules, parameters, preferences, and/or other information associated with the processing of healthcare claim transactions to the service provider computer 106 and/or the eligibility module 180.

The network 115 may include any telecommunication and/or data network, whether public, private, or a combination thereof, including a local area network, a wide area network, an intranet, the Internet, intermediate handheld data transfer devices, and/or any combination thereof and may be wired and/or wireless. The network 115 may also allow for real time, offline, and/or batch transactions to be transmitted between or among the healthcare provider computer 104, the service provider computer 106, and the claims processor computer 108. Due to network connectivity, various methodologies as described herein may be practiced in the context of distributed computing environments. Although the service provider computer 106 is shown for simplicity as being in communication with the healthcare provider computer 104 or the claims processor computer 108 via one intervening network 115, it is to be understood that any other network configuration is possible. For example, intervening network 115 may include a plurality of networks, each with devices such as gateways and routers for providing connectivity between or among networks 115. Instead of or in addition to a network 115, dedicated communication links may be used to connect the various devices in accordance with an example embodiment of the invention. For example, the service provider computer 106 may form the basis of network 115 that interconnects the healthcare provider computer 104 and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 106 (or other computer) may be implemented as a specialized processing machine that includes hardware and/or software for performing the methods described herein. In addition, at least a portion of the processor and/or processing capabilities of the service provider computer 106 and/or the eligibility module 180, may be implemented as part of a claims processor computer, such as the first claims processor computer 108a. Accordingly, embodiments of the invention should not be construed as being limited to any particular operating environment, system architecture, or device configuration.

Operational Overview

Figure 2A:
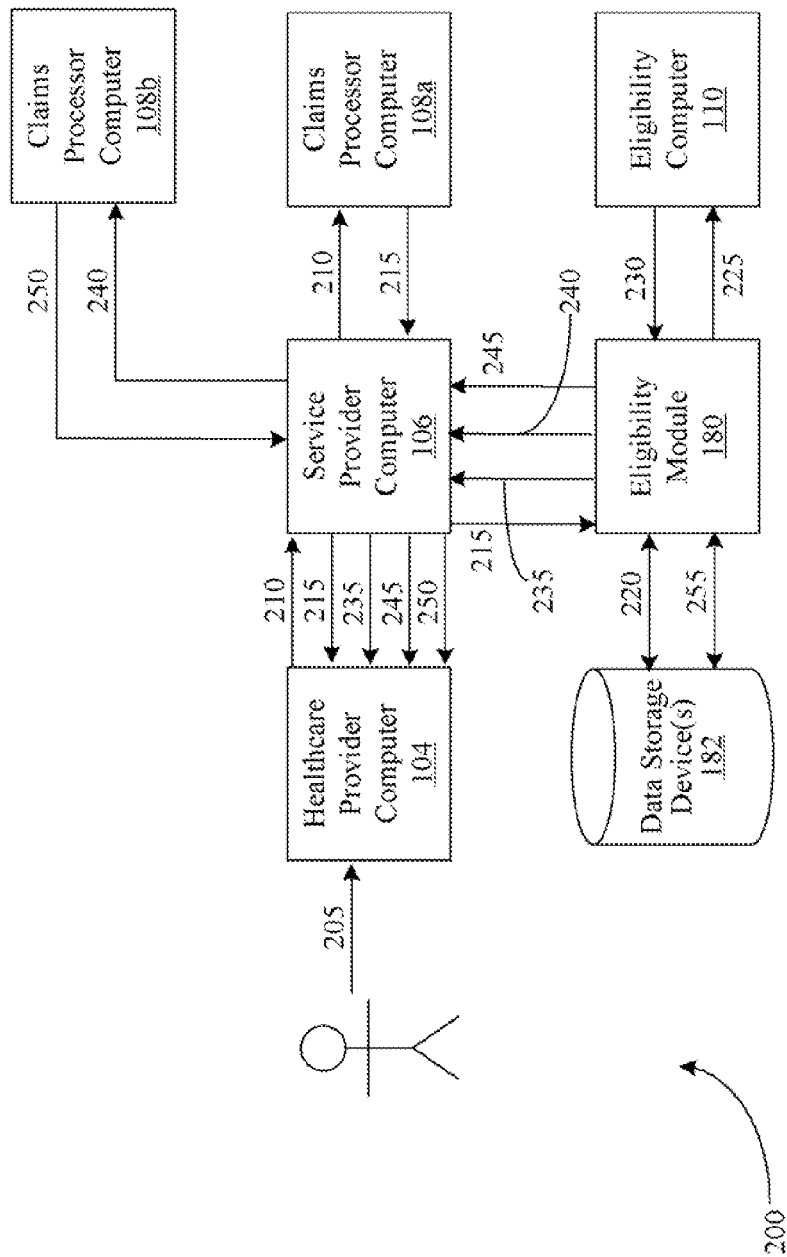
FIGS. 2A and 2B are block diagrams of example data flows for processing replies to healthcare claim transactions as they are communicated through a service provider and determining available payers for the healthcare claim transactions, according to example embodiments of the invention.

FIG. 2A is an example block diagram 200 for processing replies to healthcare claim transactions as they are communicated through a service provider, such as the service provider computer 106 illustrated in FIG. 1. With reference to FIG. 2A, a healthcare provider computer, such as the healthcare provider computer 104 illustrated in FIG. 1, may receive a healthcare request 205 from a patient. The healthcare request 205 may be a prescription order that is received in-person or electronically as desired in various embodiments of the invention. For example, a patient may seek to fill a prescription for one or more drugs, medications, and/or other products at a pharmacy location or store. As another example, a patient may communicate a healthcare request 205, such as a request to fill a prescription, to a healthcare provider computer 104 via one or more suitable network connections. For example, a purchase request may be communicated to a healthcare provider computer 104 from a customer computer via a web portal hosted by the healthcare provider computer 104. In addition, a physician/clinic/hospital computer can also communicate a healthcare request 205 as an electronic prescription order (e.g., an E-SCRIPT) to the healthcare provider computer 104.

The healthcare provider computer 104 may receive and process the request 205 to generate a healthcare transaction request 210, which may be in the form of a prescription claim request or an eligibility request. The generated healthcare transaction request 210 may be communicated by the healthcare provider computer 104 to the service provider computer 106. Accordingly, the healthcare transaction request 210 may be received by the service provider computer 106.

According to an example embodiment of the invention, the healthcare transaction request 210 may be in accordance with a version of a National Council for Prescription Drug Programs ("NCPDP") Telecommunication Standard, although other standards may be utilized as well. As desired, the healthcare transaction request 210 may include a BIN and/or PCN for identifying a claims processor computer, such as one of the claims processor computers 108a-n illustrated in FIG. 1, as a destination of the healthcare transaction request 210. In addition, the healthcare transaction request 210 may also include information relating to the patient, payer, prescriber, healthcare provider, and/or the prescribed drug or product. As an example, the healthcare transaction request 210 received by the service provider computer 106 may include one or more of the following information:

Payer ID/Routing Information for each identified payer or potential payer
  Banking Identification Number (BIN) and Processor Control Number PCN) that designates an intended destination of the healthcare transaction request 210
Patient Information
  Name (e.g., Patient Last Name, Patient First Name, etc.)
  Date of Birth of Patient
  Age of Patient
  Gender
  Patient Address (e.g., Street Address, Zip Code, etc.)
  Patient Contact Information (e.g., Patient Telephone Number)

Patient ID or other identifier
Insurance/Coverage Information
Cardholder Name (e.g., Cardholder First Name, Cardholder Last Name)
Cardholder ID and/or other identifier (e.g., person code)
Provider (e.g., Prescriber, Pharmacy) Information
Prescriber Information
Primary Care Provider ID or other identifier (e.g., National Provider Identifier (NPI) code)
Primary Care Provider Name (e.g., Last Name, First Name)
Prescriber ID or other identifier (e.g., NPI code, DEA number)
Prescriber Name (e.g., Last Name, First Name)
Prescriber Contact Information (e.g., Telephone Number)
Pharmacy or other Healthcare Provider Information (e.g., store name, chain identifier, etc.)
Pharmacy or other Healthcare Provider ID (e.g., NPI code)
Claim Information
Drug or product information (e.g., National Drug Code (NDC))
Prescription/Service Reference Number
Date Prescription Written
Quantity Dispensed
Number of Days Supply
Diagnosis/Condition
Pricing information for the drug or product (e.g., network price, Usual & Customary price)
Date of Service.

In certain embodiments, the healthcare transaction request 210 may be in the form of a prescription claim request. Accordingly, for purposes of describing the remainder of FIG. 2A, the healthcare transaction request 210 may additionally be referred to as a healthcare claim transaction 210.

The service provider computer 106 may receive the healthcare claim transaction 210 from the healthcare provider computer 104, and the service provider computer 106 may process the healthcare claim transaction 210. As desired, the service provider computer 106 may perform one or more pre-edits on the healthcare claim transaction 210. The pre-edits may verify, add, and/or edit information included in the healthcare claim transaction 210 prior to the healthcare claim transaction 210 being communicated to an appropriate claims processor computer 108. If no rejections are triggered or generated by any pre-edits performed for the transaction 210, then the healthcare claim transaction 210 and/or a copy thereof may be routed or otherwise communicated by the service provider computer 106 to an appropriate claims processor computer, such as claims processor computer 108a, associated with a designated payer for adjudication. According to an example embodiment, the service provider computer 106 may utilize at least a portion of the information included in the healthcare claim transaction 210, such as a BIN/PCN, to determine the appropriate claims processor computer 108a to route the healthcare claim transaction 210 to. The service provider computer 106 may also include a routing table, perhaps stored in memory, for determining which claims processor computer 108a to route the healthcare claim transaction 210 to.

The first claims processor computer 108a may receive and adjudicate or otherwise process the healthcare claim transaction 210. For example, the first claims processor computer 108a may determine benefits coverage for the healthcare claim transaction 210 according to an adjudication process associated with eligibility, pricing, and/or utilization review. During the adjudication process, the first claims processor computer 108a may determine that the patient associated with the healthcare claim transaction 210 is not covered by the claims processor or that coverage information for the patient is incorrect or incomplete. The first claims processor computer 108a may transmit an adjudicated reply 215 or response for the healthcare claim transaction 210 to the service provider computer 106. The adjudicated reply 215 or response may include an indication that the healthcare claim transaction 210 has been rejected for a patient eligibility reason, such as an indication that the patient is not covered by the claims processor or an indication that coverage information is incorrect or incomplete. In certain embodiments, the indication may be represented by one or more reject codes included in the adjudicated reply 215.

The service provider computer 106 may receive the adjudicated reply 215 from the first claims processor computer 108a. As desired, the service provider computer 106 may perform any number of post-edits on the adjudicated reply 215. In certain embodiments, a determination may be made as to whether a healthcare provider or group of healthcare providers associated with the transaction 210 has enabled or activated an eligibility service for use in processing adjudicated replies that are routed or otherwise communicated through the service provider computer 106. If an eligibility service is not activated, then the adjudicated reply 215 may be routed or otherwise communicated to the healthcare provider computer 104. If, however, an eligibility service is activated, then the adjudicated reply 215, a copy of the reply 215, and/or information included in the reply may be communicated to a suitable eligibility module, such as the module 180 shown in FIG. 1, for processing.

The eligibility module 180 may determine whether the adjudicated reply 215 indicates that the healthcare claim transaction 210 has been rejected for an eligibility reason. For example, the eligibility module 180 may identify one or more reject codes included in the adjudicated reply 215 and compare the identified reject code(s) to one or more stored reject codes associated with eligibility rejections. A wide variety of stored reject codes may be utilized as desired in various embodiments of the invention, such as the reject codes set forth in Table 1 above. If no match is found or the eligibility module 180 otherwise determines that the claim transaction 210 was not rejected for an eligibility reason, then the eligibility module 180 may direct the service provider computer 106 to route or otherwise communicate the adjudicated reply 215 to the healthcare provider computer 104. If, however, a match is found or the eligibility module 180 otherwise determines that the claim transaction 210 was rejected due to an eligibility reason, then the eligibility module 180 may attempt to identify an available payer or claims processor for the patient associated with the healthcare claim transaction 210.

In certain embodiments, the eligibility module 180 may search and/or access one or more suitable databases or data storage devices that include patient eligibility information, such as the databases 182 illustrated in FIG. 1. The databases 182 may be searched or accessed utilizing at least a portion of the patient identifying information included in the healthcare claim transaction 210 and/or the adjudicated reply 215. Based upon the search, a determination may be made as to whether the databases 182 include one or more records or entries that include eligibility or coverage information 220 for the patient.

In other embodiments, the eligibility module 180 may utilize at least a portion of the patient identifying information included in the healthcare claim transaction 210 and/or the adjudicated reply 215 to generate an eligibility request 225 for patient coverage and/or eligibility information. The generated eligibility request 225 may be communicated by the eligibility module 180 or the service provider computer 106 to an eligibility computer, such as the eligibility computer 110 illustrated in FIG. 1. In certain embodiments, the eligibility request 225 may be in accordance with an NCPDP format (e.g., an E1 transaction) or X12 format (e.g., a 270 transaction), although other formats or protocols could equally be utilized. The eligibility computer 110 may receive the eligibility request 225, which includes at least some of the patient information. Using the patient information, for example, a combination of the patient name, date of birth ("DOB"), zip code, and Cardholder ID, the eligibility computer 110 can determine whether the patient is associated with one or more payers. For example, the eligibility computer 110 may have access to payer information for a plurality of patients, and may identify one or more payers for a patient by matching certain patient information. If the eligibility computer 110 identifies one or more payers, then the eligibility computer 110 may provide an eligibility response 230 that identifies the one or more payers. For example, the one or more payers may be identified in the eligibility response 230 according to one or both of a respective name or a BIN/PCN. The eligibility response 230 may also identify a priority, ordering, or ranking among the payers if more than two payers are identified. The priority, ordering, or ranking may be used to determine an order in which claim requests are generated and processed by the two or more identified payers. On the other hand, if the eligibility computer 110 cannot identify any payers associated with the patient, then the eligibility response 230 may reflect that no payers have been identified for the patient.

The eligibility module 180 may analyze accessed eligibility information 220 and/or the eligibility response 230 to determine whether one or more payers are available for the patient. If multiple payers are available, then the eligibility module 180 may identify a primary payer. In this regard, the eligibility module 180 may determine whether a payer is available for resubmission of the rejected healthcare claim transaction 210. If the eligibility module 180 identifies an available payer, then the eligibility module 180 may direct the communication of information 235 associated with the identified available payer to the healthcare provider computer 104 and/or to another device or system associated with the healthcare provider, such as a suitable facsimile/printer device. A wide variety of information 235 associated with an available payer may be communicated to the healthcare provider as desired in various embodiments, including but not limited to, a name of an available payer, a BIN/PCN for an available payer, a Patient ID or Cardholder ID of the patient with the payer, a Group number of the patient, a coverage effective date, co-pay information, etc. In certain embodiments, the information 235 may be appended to the adjudicated reply 215, and the adjudicated reply 215 may be routed or otherwise communicated to the healthcare provider computer 104 by the service provider computer 106. In other embodiments, the information 235 may be communicated to the healthcare provider via one or more messages or communications that are separate from the adjudicated reply 215. As desired, the healthcare provider may utilize the information to prepare a new healthcare claim transaction or request for submission to the available payer.

In certain embodiments, the eligibility module 180 may determine whether an automatic resubmission of the rejected healthcare claim transaction 210 to an identified available payer has been authorized by the healthcare provider or a group of healthcare providers. For example, the eligibility module 180 may access processing rules and/or preferences associated with the healthcare provider or group of healthcare providers in order to determine whether an automatic resubmission has been authorized. A wide variety of rules may be accessed as desired in various embodiments, such as timing rules for resubmissions, timing thresholds for resubmissions, product or drug-specific resubmission rules, therapeutic class resubmission rules, etc. For example, in certain embodiments, a resubmission may only be authorized if the resubmission will likely be completed prior to the expiration of a timing threshold for submitting an adjudicated reply to the healthcare provider computer 104.

If the eligibility module 180 determines that resubmission has been authorized, then the eligibility module 180 may generate or build a second healthcare claim transaction 240 or healthcare claim request based upon information associated with the identified available payer (e.g., BIN/PCN, etc.) and information included in the original healthcare claim transaction 210 and/or adjudicated reply 215. The generated second claim transaction 240 or a copy thereof may then be routed or otherwise communicated by the service provider computer 106 to a claims processor computer 108b associated with the identified available payer. According to an example embodiment, the service provider computer 106 may utilize at least a portion of the information included in the second claim transaction 240, such as a BIN/PCN, to determine the appropriate claims processor computer 108b to route the second claim transaction 240 to. The service provider computer 106 may also include a routing table, perhaps stored in memory, for determining which claims processor computer 180b to route the second claim transaction 240 to. As desired in certain embodiments, a message 245 indicating that the claim transaction 210 is being resubmitted and optionally including information 235 associated with the available payer may be communicated by the eligibility module 180 and/or the service provider computer 106 to the healthcare provider computer 104 and/or another device (e.g., facsimile/printer device) associated with the healthcare provider. For example, a message indicating that the claim transaction 210 is being resubmitted may be communicated to the healthcare provider to alert the healthcare provider of a delay in processing the claim transaction 210.

As shown in FIG. 2A, the identified available payer may be a payer other than the payer that rejected the original claim transaction 210 and, therefore, the second claim transaction 240 may be communicated to a claims processor computer 108b other than the claims processor computer 108a that processed the original claim transaction 210. However, in other embodiments, the identified available payer may be the same payer that rejected the original claim transaction 210. For example, if the coverage information for the patient was incorrect or incomplete, correct coverage information for the same payer may be utilized to generate the second claim transaction 240.

With continued reference to FIG. 2A, the second claims processor computer 108b may receive and adjudicate or otherwise process the second claim transaction 240. For example, the second claims processor computer 108b may determine benefits coverage for the second claim transaction 240 according to an adjudication process associated with eligibility, pricing, and/or utilization review. The second claims processor computer 108b may transmit a second adjudicated reply 250 for the second claim transaction 240 to the service provider computer 106. The service provider computer 106 may receive the second adjudicated reply 250 from the second claims processor computer 108b. As desired, the service provider computer 106 may perform any number of post-edits on the second adjudicated reply 250 in a similar manner as that set forth above for the first adjudicated reply 215. The second adjudicated reply 250 may then be routed or otherwise communicated to the healthcare provider computer 104. In certain embodiments, the second adjudicated reply 250 may be substituted for the first adjudicated reply 215. Additionally, as desired, an indication of the substitution and/or information associated with the identified available payer may be communicated to the healthcare provider computer 104 in order to facilitate an update of information associated with the healthcare claim transaction 210 by the healthcare provider, such as an update in payer and/or coverage information.

Additionally, as desired in certain embodiments, the eligibility module 180 may be configured to store a wide variety of information 255 associated with the processing of claim transactions and/or adjudicated replies. Examples of suitable information that may be stored include, but are not limited to, information included in the first and/or second healthcare claim transaction 210, 240, information included in the first and/or second adjudicated reply 215, 250, resubmission information, eligibility information for a patient, information associated with the eligibility request 225, information associated with the processing of the first transaction 210 and/or adjudicated reply 215, information associated with the invocation of the eligibility module 180, etc. In certain embodiments, as described above with reference to FIG. 1, the eligibility module 180 and/or the service provider computer 106 may be configured to generate a wide variety of reports associated with the processing of healthcare claim transactions and/or adjudicated responses. Generated reports may then be communicated to one or more recipients, such as the healthcare provider computer 104 and/or a healthcare provider back office computer 195. A wide variety of suitable communications techniques, for example, electronic mail, short message service ("SMS") messaging, other electronic communications, snail mail, etc., may be utilized as desired to communicate generated reports to one or more recipients.

Additionally, in certain embodiments, information associated with the invocation of the eligibility module 180 may be communicated to an appropriate billing system associated with the service provider computer 106 in order to facilitate billing customers, such as healthcare providers, for the services provided by the eligibility module 180. Alternatively, the eligibility module 180 may alter a billing code or other field of the healthcare claim transaction 210 and/or adjudicated reply 215 to a value indicating that the transaction or request has been evaluated or processed by the eligibility module 180. The altered billing code may be recognized during subsequent or further processing of the healthcare claim transaction 210 or adjudicated reply 215, such as further processing by the service provider computer 106, in order to facilitate billing.

Figure 2B:
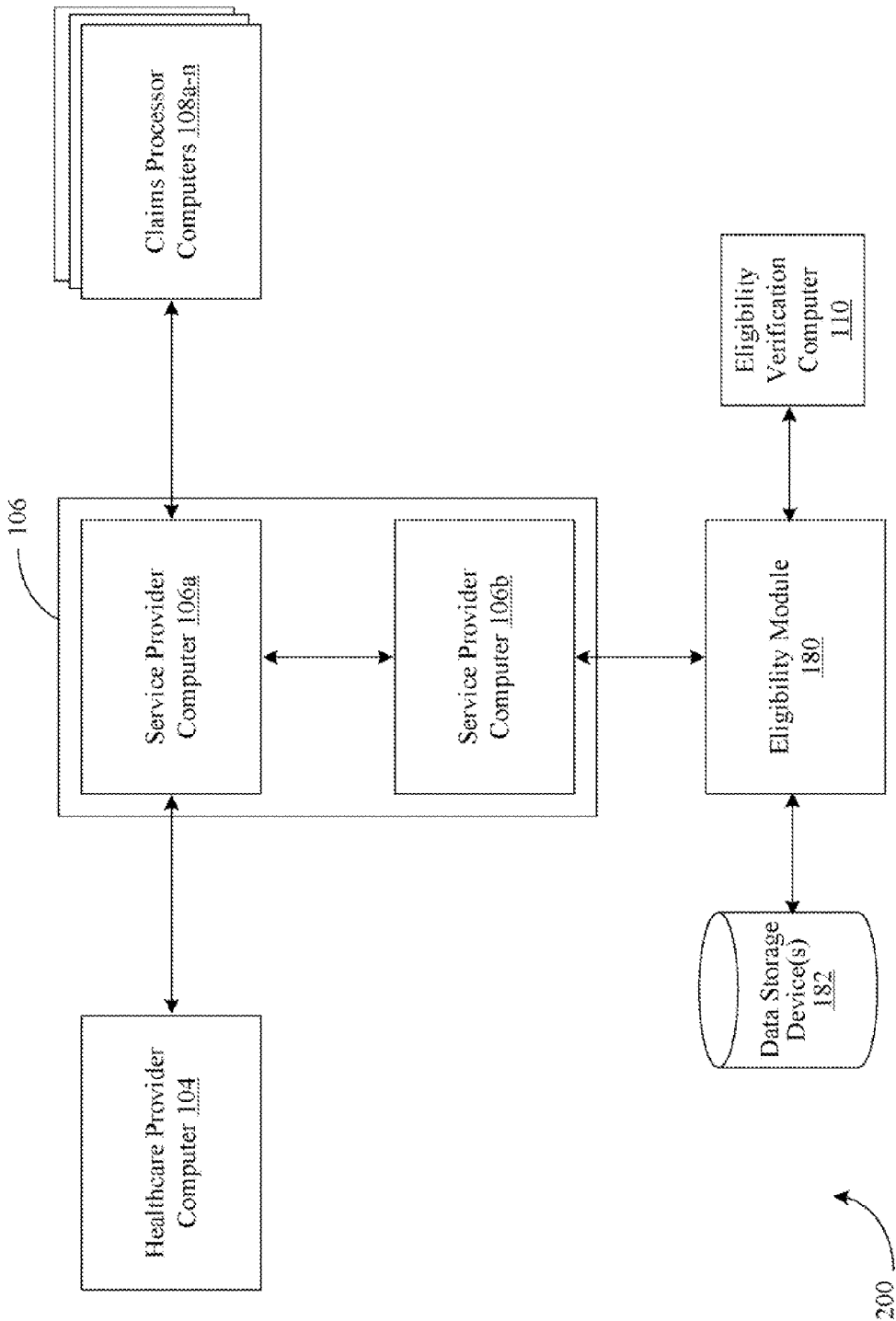

It will be appreciated that variations of the data flow 200 illustrated in FIG. 2A may be utilized in accordance with various embodiments of the invention. For example, as shown in FIG. 2B, the service provider computer 106 may be comprised of two or more distinct service provider computers 106a and 106b that are in communication with each other. Service provider computer 106a may be operative with one or more healthcare provider computers and claims processor computers, such as the healthcare provider computer 104 and claims processor computer 108 illustrated in FIG. 1. However, service provider computer 106b may have a data processing arrangement with service provider computer 106a. Under the data processing agreement, the service provider computer 106a may be permitted to utilize or offer services of the service provider computer 106b, including those of the eligibility module 180. For example, a first service provider may communicate claims and/or other information to a second service provider for processing.

As described herein, healthcare transactions and/or adjudicated replies may be examined as they are routed to or through a service provider computer 106. In this regard, an eligibility service may be provided in real time or near real time as the healthcare transactions and adjudicated replies are routed to or through the service provider computer 106. FIG. 3 is a flow diagram of an example method 300 for processing a reply to a healthcare claim transaction, according to an example embodiment of the invention. The method 300 may be performed by a suitable service provider computer and/or an associated eligibility module, such as the service provider computer 106 and the eligibility module 180 illustrated in FIG. 1. The method 300 may begin at block 305.

At block 305, an adjudicated reply or response to a healthcare claim transaction may be received from a claims processor computer, such as the claims processor computer 108 illustrated in FIG. 1. One or more post-edits and/or evaluations may be performed on the received adjudicated reply as desired in various embodiments of the invention. For example, one or more post-edits may be performed by a suitable PPE module, such as the PPE module 156 illustrated in FIG. 1.

At block 310, a determination may be made as to whether the healthcare claim transaction has been paid or approved for payment. For example, the adjudicated reply may be analyzed in order to determine whether the underlying healthcare claim transaction has been paid or approved for payment by the claims processor computer 108. If it is determined at block 310 that the claim has been paid or approved, then operations may continue at block 330 and the received adjudicated reply may be routed or otherwise communicated to a healthcare provider computer from which the healthcare claim transaction originated, such as the healthcare provider computer 104 illustrated in FIG. 1. If, however, it is determined at block 310 that the healthcare claim transaction has not been paid or that the claim transaction has been rejected, then operations may continue at block 315.

At block 315, a determination may be made as to whether or not an eligibility edit or service is enabled or activated for the healthcare claim transaction and associated adjudicated reply. For example, rules or preferences associated with processing healthcare claim transactions (e.g., rules received from the healthcare provider computer 104 and/or a healthcare provider back office computer 195) may be analyzed in order to determine whether an eligibility edit is enabled. If it is determined at block 315 that an eligibility edit is not enabled, then operations may continue at block 330 and the adjudicated reply may be routed or otherwise communicated to the healthcare provider computer 104. If, however, it is determined at block 315 that an eligibility edit is enabled, then operations may continue at block 320.

At block 320, the adjudicated reply and/or the underlying healthcare claim transaction may be processed by a suitable eligibility module 180 or eligibility application. The eligibility module 180 may, for example, determine whether an available payer can be identified for a patient associated with the healthcare claim transaction. In other words, the eligibility module 180 may determine whether a payer with which the patient has coverage can be identified. One example of the operations that may be performed by the eligibility module 180 in order to process an adjudicated reply is described in greater detail below with reference to FIG. 4.

At block 325, a determination may be made as to whether an eligibility message or other eligibility information generated by the eligibility module 180 is available. If it is determined at block 325 that an eligibility message is not available, then operations may continue at block 330 described above, and the adjudicated reply may be routed or otherwise communicated to the healthcare provider computer 104. If, however, it is determined at block 325 that an eligibility message is available, then operations may continue at block 335. At block 335, an adjudicated reply and patient eligibility information identifying an available payer for the patient may be communicated to the healthcare provider computer 104 and/or to one or more other devices associated with the healthcare provider (e.g., a facsimile/printer device). In certain embodiments, eligibility information may be appended to the adjudicated reply, and the adjudicated reply may be communicated to the healthcare provider computer 104. In other embodiments, the adjudicated reply may be communicated to the healthcare provider computer 104, and one or more separate messages that include the eligibility information may be communicated to the healthcare provider. In yet other embodiments, such as embodiments in which an automatic resubmission has been authorized, a second adjudicated reply that is received from a claims processor associated with an identified available payer may be routed or otherwise communicated to the healthcare provider computer 104 as a response to the original healthcare claim transaction. As desired, eligibility information for the patient may be appended to the second adjudicated reply and/or communicated to the healthcare provider via one or more other messages.

At block 340, which may be optional in certain embodiments of the invention, information associated with the adjudicated reply, the underlying healthcare claim transaction, processing of the adjudicated reply and/or claim transaction, eligibility information, a resubmission of the healthcare claim transaction, and/or the invocation of the eligibility module 180 may be stored and/or communicated for billing and/or reporting purposes. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the eligibility service provided by the eligibility module 180. A wide variety of different types of billing information may be stored and/or communicated as desired in various embodiments of the invention, for example, an identifier associated with the invocation of the eligibility module 180 or a billing code (e.g., a unique billing code) associated with the invocation of the eligibility module 180. As an alternative to storing or communicating billing information, the eligibility module 180 may set a billing code for a healthcare claim transaction and/or adjudicated reply to a unique billing code associated with the provided eligibility service. The unique billing code may be identified or recognized during subsequent processing of the healthcare claim transaction and/or adjudicated reply by either the billing system or a component of the service provider computer 106. The identified billing code may then be utilized by the billing system in the generation of bills for customers of the service provider.

At block 345, which may be optional in certain embodiments of the invention, one or more reports may be generated utilizing at least a portion of the stored information. Reports may be generated by the eligibility module 180, the service provider computer 106, and/or a separate reporting module. A wide variety of different information may be included in a generated report, including but not limited to, information extracted from one or more healthcare claim transactions and/or adjudicated replies, resubmission information, patient eligibility information, invocation rate information for the eligibility module 180, financial information, billing information, etc. Additionally, generated reports may be formatted and/or sorted utilizing a wide variety of different parameters and/or criteria, such as identifiers for healthcare provider computers, identifiers for healthcare providers, identifiers for products and/or services associated with healthcare claim transactions, dates of service, etc. As desired, generated reports may be communicated to one or more recipients, such as the healthcare provider computer 104 and/or the healthcare provider back office computer 195.

The method 300 may end following either block 330 or 345.

FIG. 4 is a flow diagram of an example method 400 for processing a reply to a healthcare claim transaction in order to identify an available payer for the healthcare claim transaction, according to an example embodiment of the invention. The method 400 illustrated in FIG. 4 may be an example implementation of block 320 shown in FIG. 3. As such, the method 400 may be performed by a suitable service provider computer and/or eligibility module, such as the service provider computer 106 and/or eligibility module 180 illustrated in FIG. 1. The method 400 may begin at block 405.

At block 405, information associated with an adjudicated reply or other response to a healthcare claim transaction may be received, such as a copy of the adjudicated reply or information extracted from the adjudicated reply. At block 410, one or more rejection codes or reject codes included in or otherwise associated with the adjudicated reply may be identified. For example, the adjudicated reply may be parsed or otherwise analyzed in order to identify a rejection code.

At block 415, a determination may be made as to whether eligibility processing is available for an identified rejection code or whether the identified rejection code is associated with an eligibility-based rejection. For example, in certain embodiments, an identified rejection code may be compared to one or more stored rejection codes associated with eligibility-based rejections, and the determination may be made based upon the comparison. For example, if a match is found, it may be determined that the healthcare claim transaction was rejected for an eligibility-based reason. If it is determined at block 415 that eligibility processing is not available for the identified rejection code or that the healthcare claim transaction was not rejected for an eligibility-based reason, then operations may continue at block 420. At block 420, the adjudicated reply may be marked as acceptable for routing or other communication to the healthcare provider computer 104.

If, however, it is determined at block 415 that eligibility processing is available for the identified rejection code or that the healthcare claim transaction was rejected for an eligibility-based reason, then operations may continue at block 425. At block 425, a patient associated with the adjudicated reply and/or identifying information associated with the patient may be identified. For example, the adjudicated reply and/or the underlying healthcare claim transaction may be parsed and/or otherwise analyzed in order to identify patient identifying information. A wide variety of patient identifying information, such as a patient name, patient address, date of birth, Cardholder ID, etc., may be identified as desired in various embodiments of the invention. At block 430, an eligibility request that includes at least a portion of the patient identifying information may be generated. The generated eligibility request may be delivered to a suitable eligibility computer, such as the eligibility computer 110 illustrated in FIG. 1, for processing. A response to the communicated eligibility request may also be received from the eligibility computer 110. As an alternative to or in addition to generating and communicating an eligibility request, at least a portion of the patient identifying information may be utilized to search or access a database, data storage device, or other data store of patient eligibility information.

At block 435, a determination may be made as to whether eligibility information for the patient has been found by the eligibility computer 110 and/or in a suitable database. For example, if the eligibility computer 110 identifies one or more payers available for the patient, then the eligibility computer 110 may provide an eligibility response indicating that information for the patient is available and that identifies the one or more available payers for the patient. In one example, the one or more payers may be identified in the eligibility response according to one or both of a respective name or a BIN/PCN. As desired, an eligibility response may also identify a priority, ordering, or ranking among the payers if more than two payers are identified. The priority, ordering, or ranking may be used to determine an order in which claim requests are generated and processed by the two or more identified payers. As another example, if the eligibility computer 110 cannot identify any payers associated with the patient, then the eligibility response may include an indication that no eligibility information was found for the patient. If it is determined at block 435 that no eligibility information for the patient has been found, then operations may continue at block 420 described above. If, however, it is determined at block 435 that eligibility information for the patient is available or that one or more payers for the patient are available, then operations may continue at block 440.

At block 440, a determination may be made as to whether an automatic resubmission of the healthcare claim transaction to an identified available payer has been authorized. For example, processing rules and/or parameters associated with the healthcare provider and/or a group of healthcare providers may be analyzed in order to determine whether a resubmission has been authorized. If it is determined at block 440 that an automatic resubmission has not been authorized, then operations may continue at block 445, and an eligibility message may be generated for communication to the healthcare provider. The eligibility message may include information associated with an identified available payer for the patient, such as a BIN/PCN for an available payer, and/or coverage information for the patient. In certain embodiments, the available payer may be a different payer than the payer that rejected the healthcare claim transaction. In other embodiments, such as embodiments in which incomplete or incorrect patient coverage information was included in the healthcare claim transaction, the available payer may be the same payer that rejected the healthcare claim transaction, and the eligibility message may include correct coverage information for the patient. Additionally, in certain embodiments, the eligibility message may be appended to the adjudicated reply. The information included in the eligibility message may be utilized as desired by the healthcare provider to resubmit the rejected healthcare claim transaction.

If, however, it is determined at block 440 that an automatic resubmission has been authorized, then operations may continue at block 450. At block 450, which may be optional in certain embodiments of the invention, a message indicating that the healthcare claim transaction is being resubmitted may be generated and communicated to the healthcare provider computer 104 or another device associated with the healthcare provider. At block 455, a new healthcare claim transaction or a second healthcare claim transaction may be generated utilizing at least a portion of the patient eligibility information (e.g., a BIN/PCN for an identified available payer) and at least a portion of the information included in the original healthcare claim transaction and/or adjudicated reply (e.g., product information, quantity information, healthcare provider information, etc.). The generated second claim transaction may then be routed or otherwise communicated to an appropriate claims processor computer associated with the identified available payer.

At block 460, a second adjudicated reply or response for the second healthcare claim transaction may be received. As desired, the second adjudicated reply may be substituted for the first adjudicated reply. In this regard, an adjudicated reply received from a payer with which the patient has coverage may be returned to the healthcare provider computer 104. Additionally, as desired, eligibility information and/or an indication that the healthcare claim transaction was resubmitted may be appended to the second adjudicated reply or otherwise communicated to the healthcare provider. In this regard, the healthcare provider may update its records associated with the healthcare claim transaction to reflect the appropriate payer and/or correct patient eligibility/coverage information.

The method 400 may end following either block 420, 445, or 460.

Figure 3:
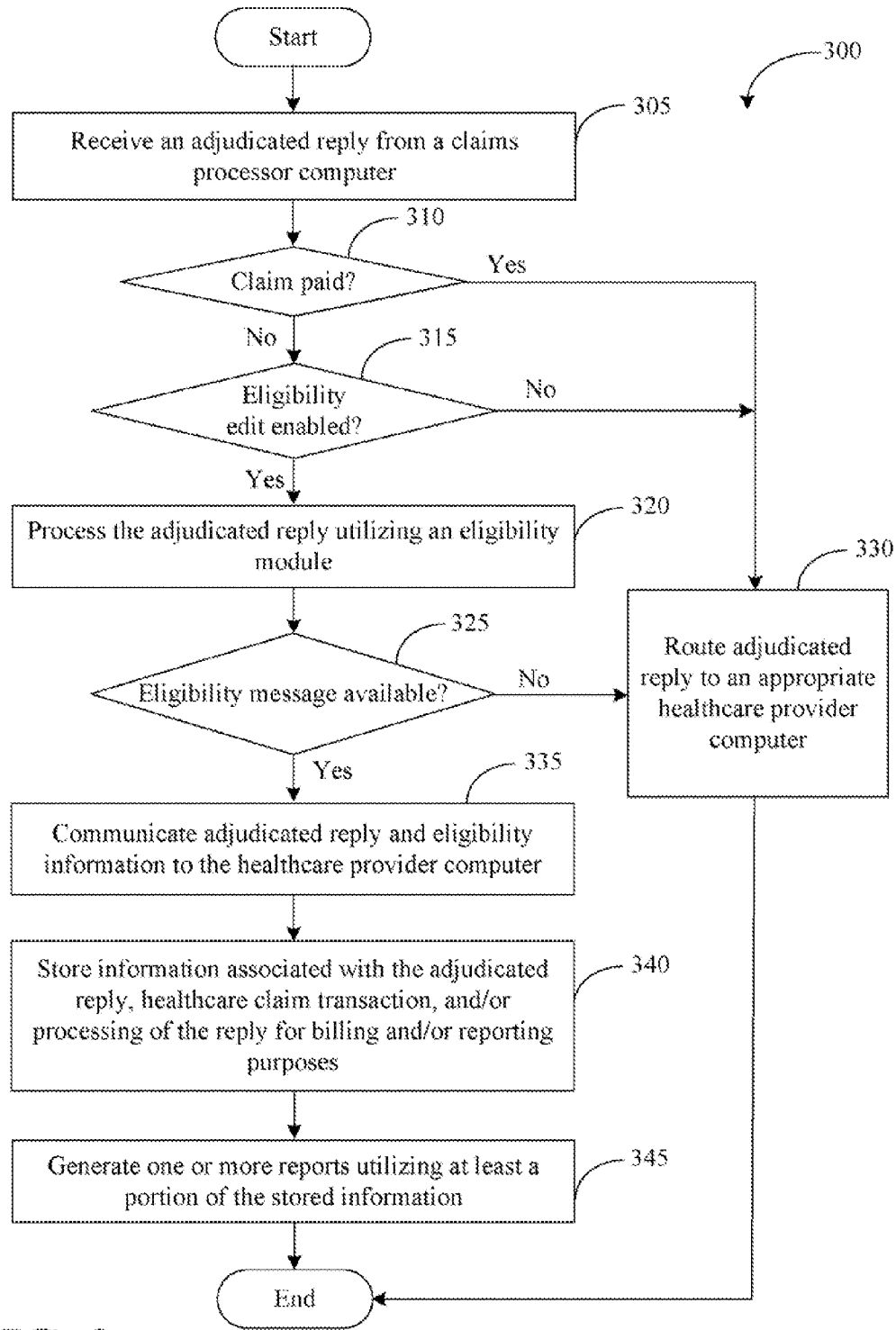
FIG. 3 is a flow diagram of an example method for processing a reply to a healthcare claim transaction, according to an example embodiment of the invention.

The operations described and shown in the methods 300 and 400 of FIGS. 3 and 4, respectively, may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3 and 4 may be performed.

Example embodiments of the invention can provide the technical effects of creating a system, method, and apparatus that identifies available payers for healthcare transactions. Additionally, example embodiments of the invention can provide the technical effect of providing patient eligibility information and/or available payer information to a healthcare provider when a previous healthcare claim transaction has been rejected. In this regard, healthcare providers can resubmit rejected healthcare claim transactions without further interaction with a patient, streamline their workflows, and improve patient satisfaction.

Various block and/or flow diagrams of systems, methods, apparatuses, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method, comprising:
    receiving, by a service provider system comprising one or more computers, a reply to a healthcare claim transaction from a claims processor computer;
    determining, by the service provider system based at least in part on an evaluation of the reply, that the healthcare claim transaction has been rejected for an eligibility reason indicating either that a patient associated with the healthcare claim transaction is not covered for benefits or that incorrect coverage information was included in the healthcare claim transaction;
    generating an eligibility request for the patient;
    communicating the eligibility request to an eligibility system;
    identifying, by the service provider system based at least in part on the determination that the healthcare claim transaction was rejected for an eligibility reason and a response to the eligibility request, an available payer for the patient; and
    communicating, by the service provider system, information associated with the identified available payer to a healthcare provider associated with the healthcare claim transaction.

2. The method of claim 1, wherein communicating information associated with the identified payer comprises:
    appending the information to the reply; and
    communicating the reply to a healthcare provider computer associated with the healthcare provider.

3. The method of claim 1, wherein determining that the healthcare claim transaction has been rejected for an eligibility reason comprises:
    identifying a reject code included in the received reply;
    comparing the identified reject code to one or more stored reject codes associated with eligibility rejections; and
    determining, based upon the comparison, that the healthcare claim transaction has been rejected for an eligibility reason.

4. The method of claim 3, wherein comparing the identified reject code to one or more stored reject codes comprises comparing the identified reject code to at least one of (i) a reject code for a missing or incomplete Banking Identification Number (BIN), (ii) a reject code for a missing or incomplete group number, (iii) a reject code for a missing or incomplete cardholder identifier, (iv) a reject code indicating that the healthcare claim transaction should be submitted to another processor, (v) a reject code for an unmatched group number, (vi) a reject code for an unmatched cardholder identifier, (vii) a reject code indicating that the patient is not covered, or (viii) a reject code indicating that the patient's coverage has expired.

5. The method of claim 1, wherein the healthcare claim transaction comprises a first healthcare claim transaction, and further comprising:
    generating, by the service provider system a second healthcare claim transaction on behalf of the patient; and
    communicating, by the service provider system, the second healthcare claim transaction to a claims processing system associated with the identified available payer.

6. The method of claim 5, wherein the claims processor computer comprises a first claims processor computer associated with a first payer, and wherein communicating the second healthcare claim transaction to a claims processing system associated with the identified available payer comprises communicating the second healthcare claim transaction to one of (i) the first claims processor computer or (ii) a second claims processor computer associated with a second payer.

7. The method of claim 5, wherein the reply comprises a first reply, and further comprising:
    receiving, by the service provider system from the claims processing system in response to the second healthcare claim transaction, a second reply; and
    communicating, by the service provider system, the received second reply to a healthcare provider computer associated with the healthcare provider.

8. The method of claim 5, further comprising:
    communicating, by the service provider system, a message to the healthcare provider indicating that the first healthcare claim transaction is being resubmitted.

9. A system, comprising:
    at least one memory operable to store computer-executable instructions; and
    at least one processor configured to access the at least one memory and execute the computer-executable instructions to:
        receive a reply to a healthcare claim transaction from a claims processor computer;
        determine, based at least in part on an evaluation of the reply, that the healthcare claim transaction has been rejected for an eligibility reason indicating either that a patient associated with the healthcare claim transaction is not covered for benefits or that incorrect coverage information was included in the healthcare claim transaction;

generate an eligibility request for the patient;

direct the communication of the eligibility request to an eligibility system;

identify, based at least in part on the determination that the healthcare claim transaction was rejected for an eligibility reason and a response to the eligibility request, an available payer for the patient; and direct the communication of information associated with the identified available payer to a healthcare provider associated with the healthcare claim transaction.

10. The system of claim 9, wherein the at least one processor is configured to direct the communication of information associated with the identified available payer by executing the computer-executable instructions to:

append the information to the reply; and direct the communication of the reply to a healthcare provider computer associated with the healthcare provider.

11. The system of claim 9, wherein the at least one processor is configured to determine that the healthcare claim transaction has been rejected for an eligibility reason by executing the computer-executable instructions to:

identify a reject code included in the received reply;

compare the identified reject code to one or more stored reject codes associated with eligibility rejections; and determine, based upon the comparison, that the healthcare claim transaction has been rejected for an eligibility reason.

12. The system of claim 11, wherein the one or more stored reject codes comprise at least one of (i) a reject code for a missing or incomplete Banking Identification Number (BIN), (ii) a reject code for a missing or incomplete group number, (iii) a reject code for a missing or incomplete cardholder identifier, (iv) a reject code indicating that the healthcare claim transaction should be submitted to another processor, (v) a reject code for an unmatched group number, (vi) a reject code for an unmatched cardholder identifier, (vii) a reject code indicating that the patient is not covered, or (viii) a reject code indicating that the patient's coverage has expired.

13. The system of claim 9, wherein the healthcare claim transaction comprises a first healthcare claim transaction, and wherein the at least one processor is further configured to execute the computer-executable instructions to:

generate a second healthcare claim transaction on behalf of the patient; and direct communication of the second healthcare claim transaction to a claims processing system associated with the identified available payer.

14. The system of claim 13, wherein the claims processor computer comprises a first claims processor computer associated with a first payer, and wherein the claims processing system associated with the identified available payer comprises one of (i) the first claims processor computer or (ii) a second claims processor computer associated with a second payer.

15. The system of claim 13, wherein the reply comprises a first reply, and wherein the at least one processor is further configured to execute the computer-executable instructions to:

receive, from the claims processing system in response to the second healthcare claim transaction, a second reply; and direct the communication of the received second reply to a healthcare provider computer associated with the healthcare provider.

16. The system of claim 13, wherein the at least one processor is further configured to execute the computer-executable instructions to:

direct the communication of a message to the healthcare provider indicating that the first healthcare claim transaction is being resubmitted.

17. A method, comprising:

receiving, by a service provider system comprising one or more computers, a reply to a healthcare claim transaction from a claims processor computer;

generating, by the service provider system based at least in part upon a determination that the healthcare claim transaction has been rejected for an eligibility reason, an eligibility request for a patient associated with the healthcare claim transaction;

communicating, by the service provider system, the eligibility request to an eligibility system;

identifying, by the service provider system based at least in part upon a response to the eligibility request received from the eligibility system, an available payer for the patient; and communicating, by the service provider system, information associated with the identified available payer to a healthcare provider associated with the healthcare claim transaction.

18. The method of claim 17, wherein generating an eligibility request based upon a determination that the healthcare claim transaction has been rejected comprises:

identifying a reject code included in the received reply;

comparing the identified reject code to one or more stored reject codes associated with eligibility rejections;

determining, based upon the comparison, that the healthcare claim transaction has been rejected for an eligibility reason; and generating the eligibility request based upon the determination that the healthcare claim transaction has been rejected for an eligibility reason.

* * * * *